(12) United States Patent
White et al.

(10) Patent No.: US 11,120,396 B2
(45) Date of Patent: *Sep. 14, 2021

(54) SYSTEM, METHOD AND APPARATUS FOR MANAGING PHARMACY INVENTORIES

(71) Applicant: SUPPLYLOGIX, LLC, Westlake, TX (US)

(72) Inventors: Charles D. White, Bedford, TX (US); Mark B. Wilgus, Colleyville, TX (US); John J. Jurek, Coon Rapids, MN (US); Daniel Z Parrish, Plano, TX (US)

(73) Assignee: SUPPLYLOGIX, LLC, Westlake, TX (US)

( * ) Notice: Subject to any disclaimer, the term of this patent is extended or adjusted under 35 U.S.C. 154(b) by 222 days.

This patent is subject to a terminal disclaimer.

(21) Appl. No.: 15/845,925

(22) Filed: Dec. 18, 2017

(65) Prior Publication Data

US 2018/0108099 A1   Apr. 19, 2018

Related U.S. Application Data

(63) Continuation of application No. 13/627,472, filed on Sep. 26, 2012, now Pat. No. 9,904,965.

(51) Int. Cl.
*G06Q 10/00* (2012.01)
*G06Q 10/08* (2012.01)
*G16H 20/10* (2018.01)
*G16H 40/20* (2018.01)

(52) U.S. Cl.
CPC .......... *G06Q 10/087* (2013.01); *G16H 20/10* (2018.01); *G16H 40/20* (2018.01)

(58) Field of Classification Search
None
See application file for complete search history.

(56) References Cited

U.S. PATENT DOCUMENTS

| | | | |
|---|---|---|---|
| 6,311,178 B1 | 10/2001 | Bi et al. | |
| 7,792,889 B1 * | 9/2010 | Lee et al. | 707/948 |
| 8,606,656 B1 * | 12/2013 | Franklin et al. | 705/27.1 |
| 9,904,965 B2 | 2/2018 | White et al. | |
| 2002/0156797 A1 * | 10/2002 | Lee et al. | 707/200 |
| 2003/0110063 A1 * | 6/2003 | Among et al. | 705/6 |
| 2004/0117383 A1 * | 6/2004 | Lee et al. | 707/100 |
| 2007/0112730 A1 | 5/2007 | Gulli et al. | |
| 2007/0174144 A1 | 7/2007 | Borders et al. | |
| 2008/0078828 A1 | 4/2008 | Helmin et al. | |

(Continued)

*Primary Examiner* — Fateh M Obaid
(74) *Attorney, Agent, or Firm* — Chalker Flores, LLP; Daniel J. Chalker

(57) ABSTRACT

A system, apparatus and method manages a product inventory of two or more vendors. A demand for each product at each vendor is determined based on a product utilization data stored in one or more databases. One or more product transfers are generated based on the demand for each product at each vendor and a product inventory data stored in the one or more databases. The one or more product transfers are bundled together by vendor-to-vendor pairings. Each transfer bundle is provided to the vendors identified in the transfer bundles. An approval, a modification or a denial is received for each transfer bundle from the vendors identified in the transfer bundles. One or more transfer orders are created for the transfer bundles that are approved and modified.

28 Claims, 11 Drawing Sheets

(56) References Cited

U.S. PATENT DOCUMENTS

| | | |
|---|---|---|
| 2009/0112687 A1* | 4/2009 | Blair et al. .................... 705/10 |
| 2009/0234848 A1 | 9/2009 | Leff et al. |
| 2010/0138281 A1 | 6/2010 | Zhang et al. |
| 2010/0169361 A1 | 7/2010 | Chen et al. |
| 2011/0257991 A1* | 10/2011 | Shukla ............................ 705/2 |
| 2013/0226699 A1* | 8/2013 | Long .......................... 705/14.53 |

* cited by examiner

SYSTEM, METHOD AND APPARATUS FOR MANAGING PHARMACY INVENTORIES

PRIORITY CLAIM AND CROSS-REFERENCE TO RELATED APPLICATIONS

This patent application is a continuation application of U.S. patent application 13/627,472 filed on Sep. 26, 2012, and entitled "System, Method and Apparatus for Managing Pharmacy Inventories", which is hereby incorporated by reference in its entirety.

FIELD OF THE INVENTION

The present invention relates generally to the field of product inventory and, more particularly, to a system, method and apparatus for managing pharmacy inventories.

BACKGROUND OF THE INVENTION

Most pharmacy inventory redistribution or rebalancing systems are "pull" type systems that rely heavily on the pharmacists operating the systems and listing their drugs on an open or closed marketplace. These systems also require the pharmacists to take action in order to purchase products. Accordingly, these systems do not meet their theoretical efficiencies or effectiveness because they are only as good as the data and effort provided by the pharmacists, who are typically overworked and are trying to satisfy the needs of their customers. Moreover, pharmacy inventory management systems focus heavily on moving inventory having short expiration dates to the exclusion of other important factors. As a result, there is a need for a system, method and apparatus that reduces the pharmacist's time and effort required to efficiently and effectively manage their inventories.

SUMMARY OF THE INVENTION

The present invention provides an inventory management system that reduces the pharmacist's time and effort required to efficiently and effectively manage their inventories. The present invention may be operated in a push mode, a pull mode or a combination of both. The present invention provides a messaging system that requests peer-to-peer inventory transfers, which can be accepted, denied or modified by the participating pharmacies.

More specifically, the present invention provides a method for managing a product inventory of two or more vendors using a computer having an interface, one or more databases and a processor communicably coupled to the interface and the one or more databases. A demand for each product at each vendor is determined based on a product utilization data stored in one or more databases. One or more product transfers are generated based on the demand for each product at each vendor and a product inventory data stored in the one or more databases. The one or more product transfers are bundled together by vendor-to-vendor pairings. Each transfer bundle is provided to the vendors identified in the transfer bundles. An approval, a modification or a denial is received for each transfer bundle from the vendors identified in the transfer bundles. One or more transfer orders are created for the transfer bundles that are approved and modified. The foregoing method can be implemented as a computer program embodied on a non-transitory computer readable medium for execution by a computer or processor such that the steps are implemented as one or more code segments.

In addition, the present invention provides an apparatus that includes a communications interface, a memory, one or more databases, and one or more processors communicably coupled to the communications interface, the memory and the one or more databases. The one or more processors determine a demand for each product at each vendor based on a product utilization data stored in the one or more databases, and generating one or more product transfers based on the demand for each product at each vendor and a product inventory data stored in the one or more databases. The one or more processors then bundle the one or more product transfers by vendor-to-vendor pairings, and provides each transfer bundle to the vendors identified in the transfer bundles. An approval, a modification or a denial is received for each transfer bundle from the vendors identified in the transfer bundles. Thereafter, the one or more processors create one or more transfer orders for the transfer bundles that are approved and modified.

The present invention also provides a system that includes one or more vendor devices, one or more communication networks, and a data processing device. The data processing device includes a communications interface communicably coupled to the one or more vendor devices via the one or more communication networks, a memory, one or more databases, and one or more processors communicably coupled to the communications interface, the memory and the one or more databases. The one or more processors determine a demand for each product at each vendor based on a product utilization data stored in the one or more databases, and generating one or more product transfers based on the demand for each product at each vendor and a product inventory data stored in the one or more databases. The one or more processors then bundle the one or more product transfers by vendor-to-vendor pairings, and provides each transfer bundle to the vendors identified in the transfer bundles. An approval, a modification or a denial is received for each transfer bundle from the vendors identified in the transfer bundles. Thereafter, the one or more processors create one or more transfer orders for the transfer bundles that are approved and modified.

The present invention is described in detail below with reference to the accompanying drawings.

BRIEF DESCRIPTION OF THE DRAWINGS

The above and further advantages of the invention may be better understood by referring to the following description in conjunction with the accompanying drawings, in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. The discussion herein relates primarily to pharmacies and pharmaceutical products, but it will be understood that the concepts of the present invention are applicable to any type of product or inventory.

The present invention provides an inventory management system that reduces the pharmacist's time and effort required to efficiently and effectively manage their inventories. The present invention may be operated in a push mode, a pull mode or a combination of both. The present invention provides a messaging system that requests peer-to-peer inventory transfers, which can be accepted, denied or modified by the participating pharmacies.

Unlike many inventory management systems, the present invention does not rely on expiration dates to identify product redistribution opportunities. Instead, the present invention concentrates on keeping products moving in each pharmacy, moving slow or non-moving products to other pharmacies where they can be consumed, and letting the expired drugs 'drop out' through pharmacy identification. The anticipated usage or demand at the candidate destination store is identified and non-moving products at other vendors are matched with that demand. Note that the automatic substitution of equivalent products is allowed if an identified shortage exists. Transfer batches are then created and optimized to minimize shipping costs. The present invention is often used with pharmacies within the same chain. Although, the present invention can be used in either a "push" or "pull" mode, the present invention is optimally operated in a "push" mode operated by chain HQ, not the pharmacists themselves, where the individual endpoints must opt-in to a transfer. No action is required by the destination store to "purchase" the product. Moreover, there is no requirement for the products to be being "listed" on an open or closed marketplace.

Figure 1:
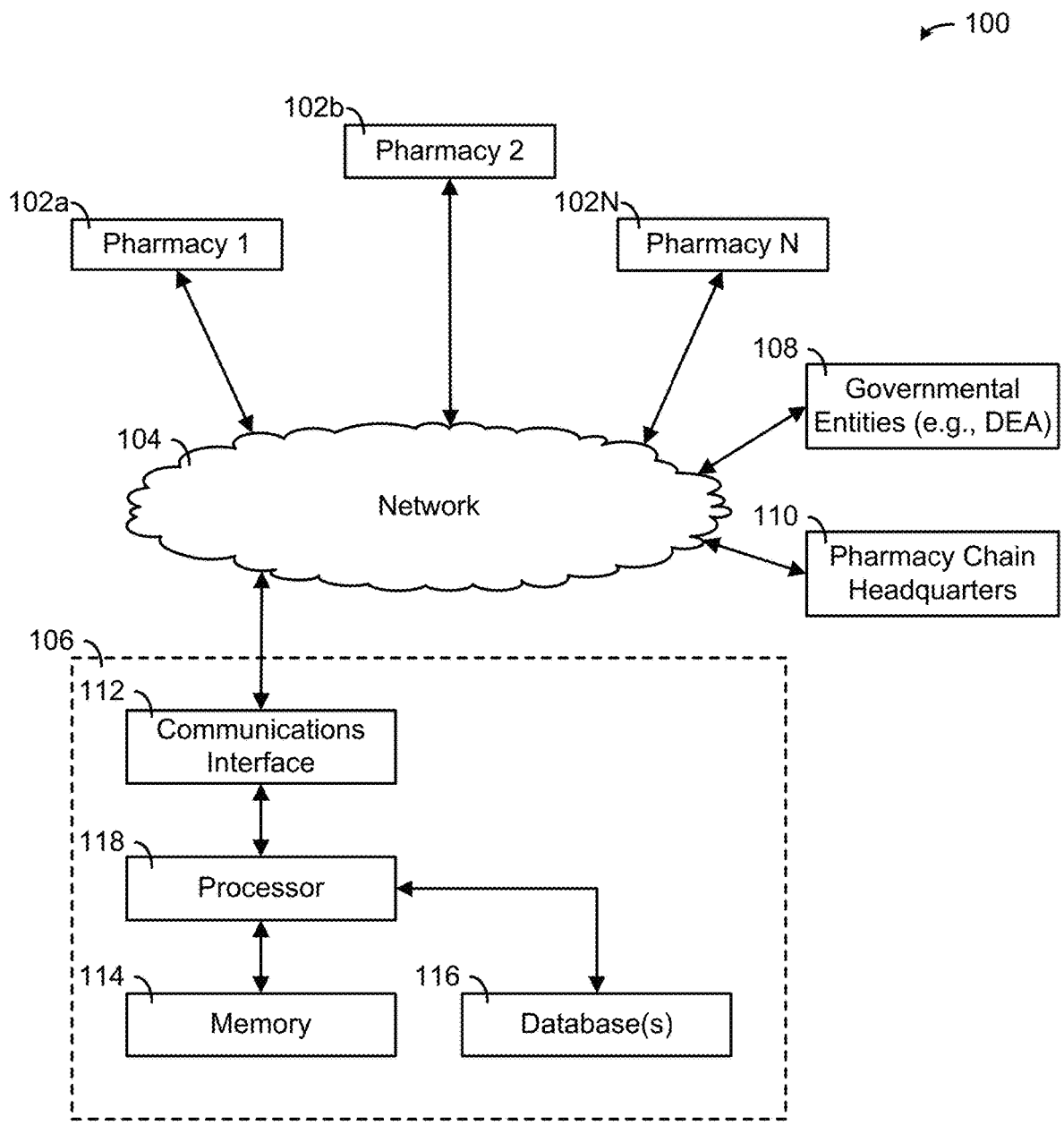
FIG. 1 is a block diagram of an inventory management system and apparatus in accordance with one embodiment of the present invention.

Referring now to FIG. 1, a block diagram of an inventory management system 100 and apparatus 106 in accordance with one embodiment of the present invention is shown. The system 100 includes two or more pharmacies 102 (e.g., Pharmacy 1—102a, Pharmacy 2—102b, Pharmacy N—102N), one or more communication networks 104 and a data processing device 106. Each pharmacy 102 communicates with the one or more communication networks 104 using a computer, a laptop, a server, a handheld computer, a mobile communications device, or any other device in which the pharmacy can communicate with the data processing device 106. The one or more communications networks 106 may include a local area network, a wide area network, a hardline connection, a wireless connection, a satellite connection, a point-to-point connection, the Internet, a private network, a service provider's network, any other means of transmitting data, or any combination thereof.

In cases where drug inventories and transfers (e.g., controlled substances) are monitored by one or more governmental entities 108, such as the Drug Enforcement Agency (DEA), the one or more governmental entities 108 communicates with the one or more communication networks 104 using a computer, a laptop, a server, a handheld computer, a mobile communications device, or any other device in which the one or more governmental entities 108 can communicate with the data processing device 106 and/or the pharmacies 102. The data processing device 106 may be operated by a pharmacy chain inventory manager or headquarters, or by a third party. If the pharmacies 102 are part of a pharmacy chain or group, which is not required, and the data processing device 106 is operated by a third party, a pharmacy chain inventory manager or headquarters 110 communicates with the one or more communication networks 104 using a computer, a laptop, a server, a handheld computer, a mobile communications device, or any other device in which the pharmacy chain inventory manager or headquarters 110 can communicate with the data processing device 106 and/or the pharmacies 102.

The data processing device 106 includes a communications interface 112, a memory 114, one or more databases 116, and one or more processors 118. The communications interface 112 is communicably coupled to the two or more pharmacies 102 and/or the one or more governmental entities 108 and/or the pharmacy chain inventory manager or headquarter 110 via the one or more communication networks 106. The communications interface 110 can be multiple interfaces, such as a query interface and a data interface. The processor 118 is communicably coupled to the communications interface 112, the memory 114 and the database(s) 116. The databases 116 may include multiple databases (e.g., a first database for the product inventory data, a second database for the product sales data, and a third database for the product availability queries and the search results). The databases 116 can be integrated into the same device as the processor 118, located locally and communicably connected to the processor 118, located remotely and communicably connected to the processor 118, or a combination thereof. Moreover, the present invention may include redundant devices or devices operating in parallel.

As will be described in more detail below, the present invention provides a computer facilitated messaging system, apparatus and method for requesting peer-to-peer transfers of inventory. The inventory transfer request messaging system, apparatus and method may operate in either of two modes: centrally orchestrated peer-to-peer transfer requests (push) or peer initiated requests for inventory transfers (pull). When using push mode transfers, the system employs optimization algorithms to maximize utilization of nonproductive inventory at destination stores while simultaneously batching products between store pairs to minimize logistics costs. An interface is provided to allow participating entities to accept or decline the transfer request. The system tracks the anticipated future usage of products and calculates a target inventory allocation for use with the proposed transfer quantity. Moreover, the interface allows an entity to adjust suggested transfer amounts upward or downward depending on local needs and anticipated demand.

Figure 2:
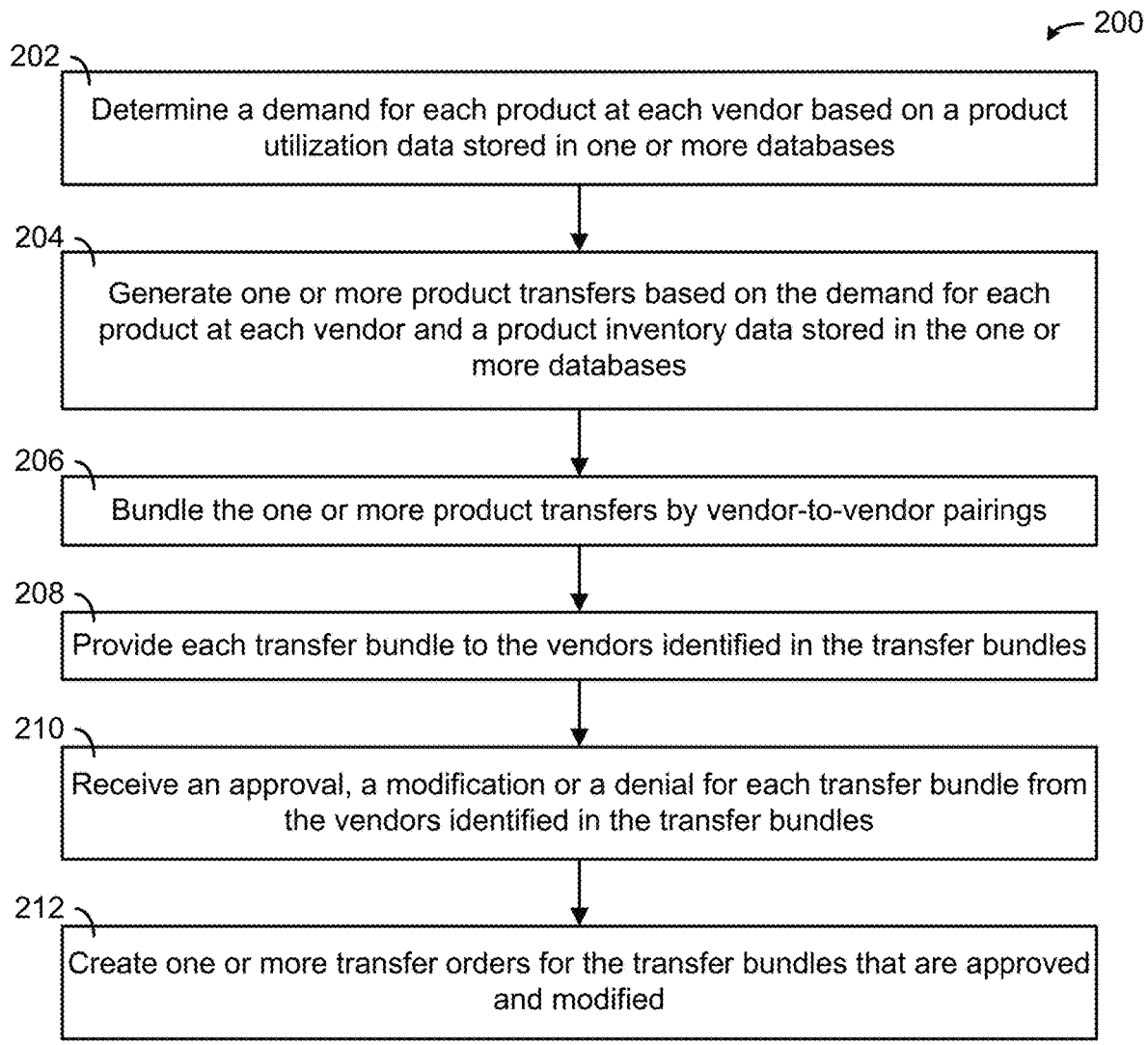
FIG. 2 is a flow chart of an inventory management process in accordance with one embodiment of the present invention.

Now referring to FIG. 2, a flow chart of an inventory management process 200 in accordance with one embodiment of the present invention is shown. The present invention provides a method for managing a product inventory of two or more vendors using a computer having an interface, one or more databases and a processor communicably coupled to the interface and the one or more databases. A demand for each product at each vendor is determined based on a product utilization data stored in one or more databases in block 202. One or more product transfers are generated based on the demand for each product at each vendor and a product inventory data stored in the one or more databases in block 204. The one or more product transfers are bundled together by vendor-to-vendor pairings in block 206. Each transfer bundle is provided to the vendors identified in the transfer bundles in block 208. An approval, a modification or a denial is received for each transfer bundle from the vendors identified in the transfer bundles in block 210. One or more transfer orders are created for the transfer bundles that are approved and modified in block 212. The foregoing method can be implemented as a computer program embodied on a non-transitory computer readable medium for execution by a computer or processor such that the steps are implemented as one or more code segments.

The system allows a wide variety of product search criteria, such as product description, product identifier code, product class, source store, destination store, etc. Any of the identifiable characteristics of a product may be used as a means of inclusion or exclusion in the redistribution search. Candidate products for redistribution may be selected based on the following criteria: slow or non-moving status, overstock status, specific product cost or product-class cost, product refrigeration status, minimum or maximum transfer unit value, minimum or maximum transfer batch value, least cost logistics site pairing, regulatory requirements governing shipment of controlled products between stores in different states, or other criteria.

Figure 3:
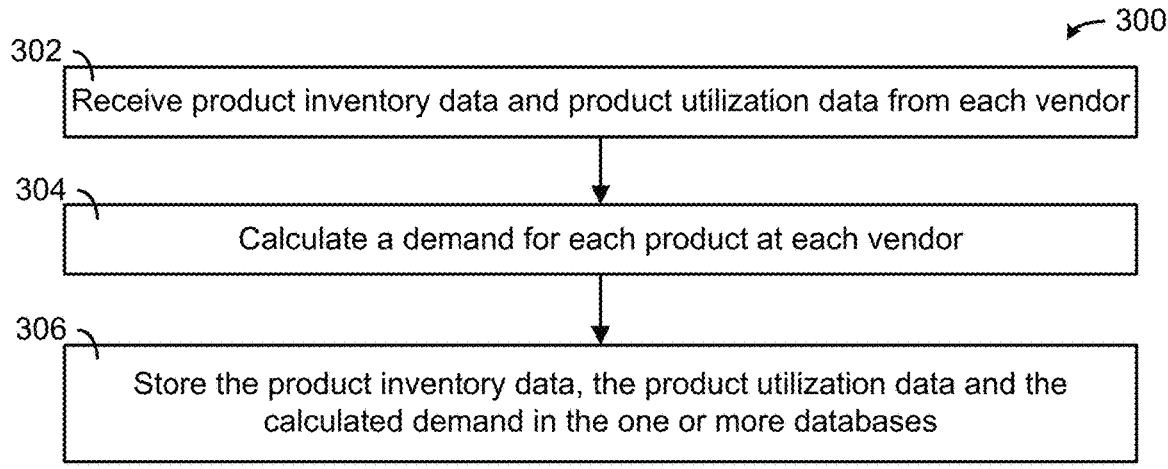
FIG. 3 is a flow chart of a database update process in accordance with one embodiment of the present invention.

Referring now to FIG. 3, a flow chart of a database update process in accordance with one embodiment of the present invention is shown. Product inventory data and product utilization data are received from each vendor in block 302 and a demand for each product at each vendor is calculated in block 304. Note a process for calculating demand without using the product inventory data is shown and described in FIGS. 10-11. The product inventory data, the product utilization data and the calculated demand are stored in the one or more databases in block 306. Note that the foregoing method can be incorporated into the method described in FIGS. 4 A-B below. Moreover, the foregoing method can be implemented as a computer program embodied on a non-transitory computer readable medium for execution by a computer or processor such that the steps are implemented as one or more code segments.

Figure 4A:
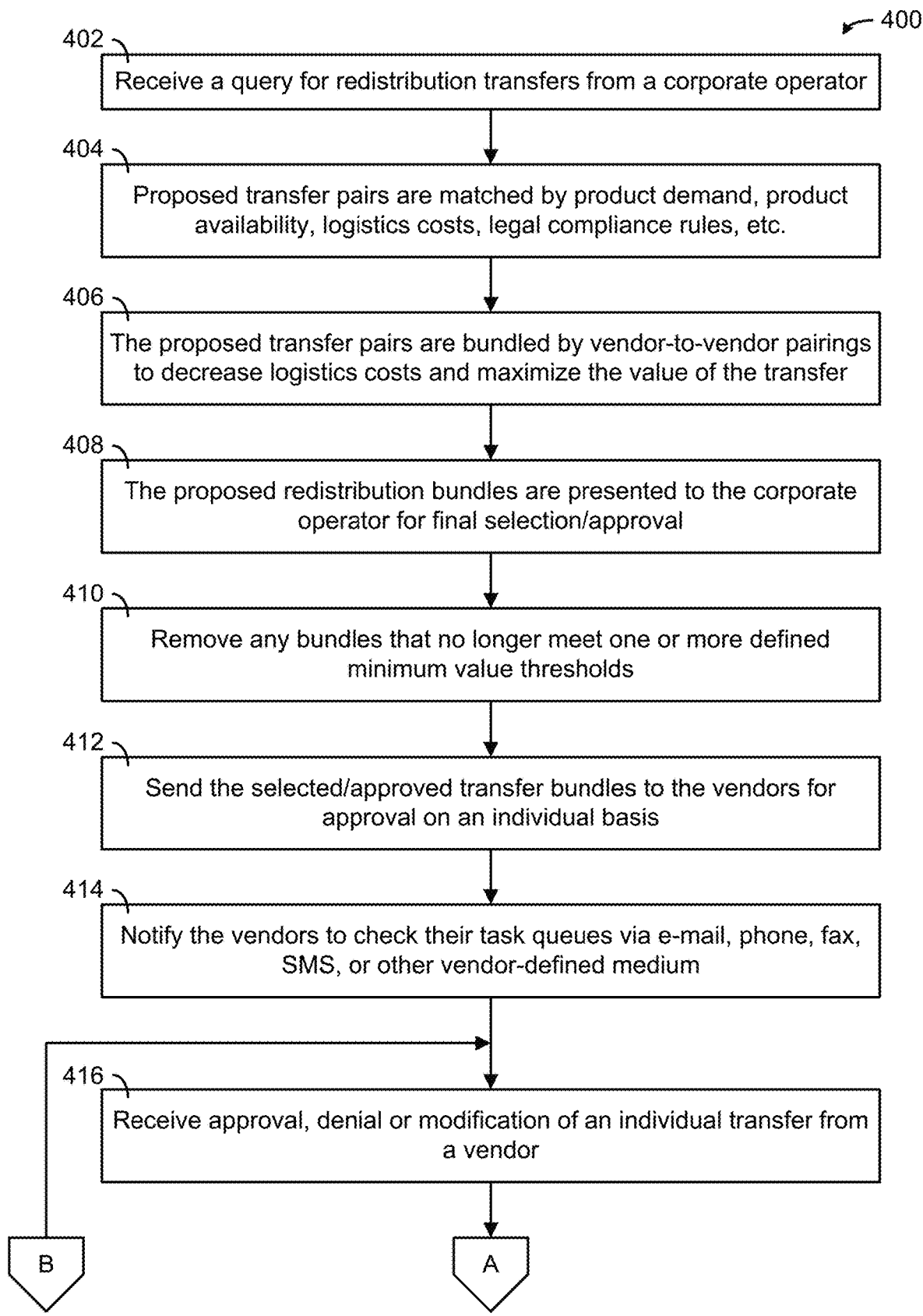
FIGS. 4A-B are flow charts of a product redistribution process in accordance with one embodiment of the present invention.
Figure 4B:
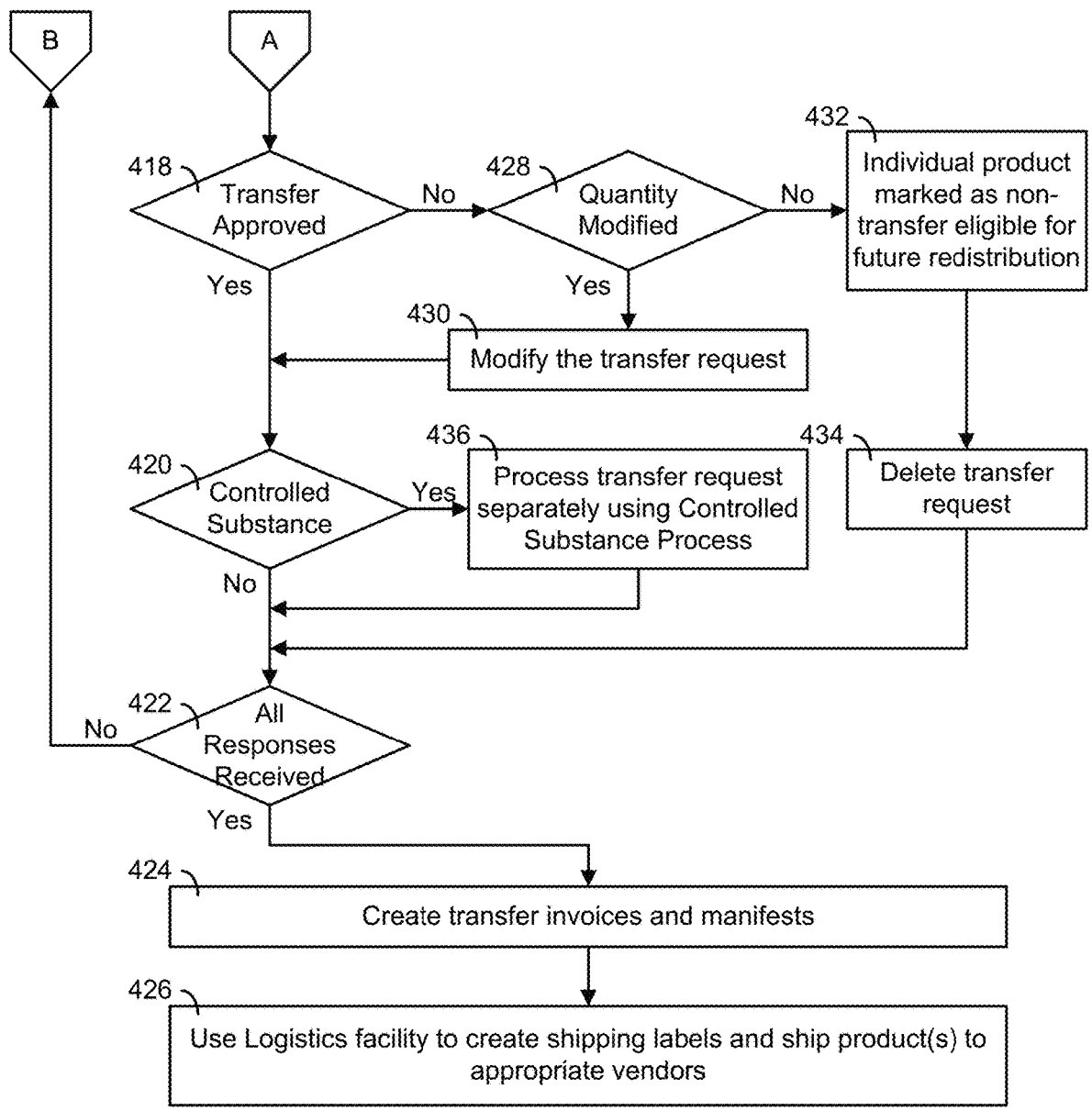

Now referring to FIGS. 4A-B, flow charts of a product redistribution process 400 in accordance with one embodiment of the present invention are shown. A query for redistribution transfers is received from a corporate operator in block 402. Proposed transfer pairs are matched by product demand, product availability, logistics costs, legal compliance rules or other desired metrics in block 404. The proposed transfer pairs are bundled by vendor-to-vendor pairings to decrease logistics costs and maximize the value of the transfer in block 406. The proposed redistribution bundles are presented to the corporate operator for final selection/approval in block 408. Any bundles that no longer meet one or more defined minimum thresholds are removed in block 410. The selected/approved transfer bundles are sent to the vendors for approval on an individual basis in block 412. The vendor approval process is shown and described in FIG. 6. The vendors are also notified to check their task queues via electronic mail, phone, fax, SMS, or other vendor-defined medium in block 414.

An approval, denial, or modification of an individual transfer is received from a vendor in block 416. If the transfer is approved, as determined in decision block 418, the product is not a controlled substance, as determined in decision block 410, and all the responses have been received, as determined in decision block 422, the transfer invoices and manifests are created in block 424. A logistics facility is used to create shipping labels and ship the product(s) to the appropriate vendors in block 426. If, however, the transfer is not approved, as determined in decision block 418, and the quantity is modified, as determined in decision block 428, the quantity in the transfer request is modified in block 430 and the process then proceeds to decision block 420. If, however, the quantity is not modified, as determined in decision block 428, the individual product is marked as non-transfer eligible for future redistribution in block 432, the transfer request is deleted in block 434 and the process then proceeds to decision block 422. If, however, the product is a controlled substance, as determined in decision block 420, the transfer request is processed separately in lock 436 using the controlled substance process shown and described in FIG. 5. If, however, all responses have not been received, as determined in decision block 422, the process loops back to block 416 where the next approval, denial or modification of the individual transfer is received and processed as previously described. Note that at some point, the system may send reminders or prompt vendors that have not responded to the individual transfer requests. "Stale" or individual transfer requests that have not be processed by the individual vendors may also be assumed to be denied and deleted after a specified period of time.

Figure 5:
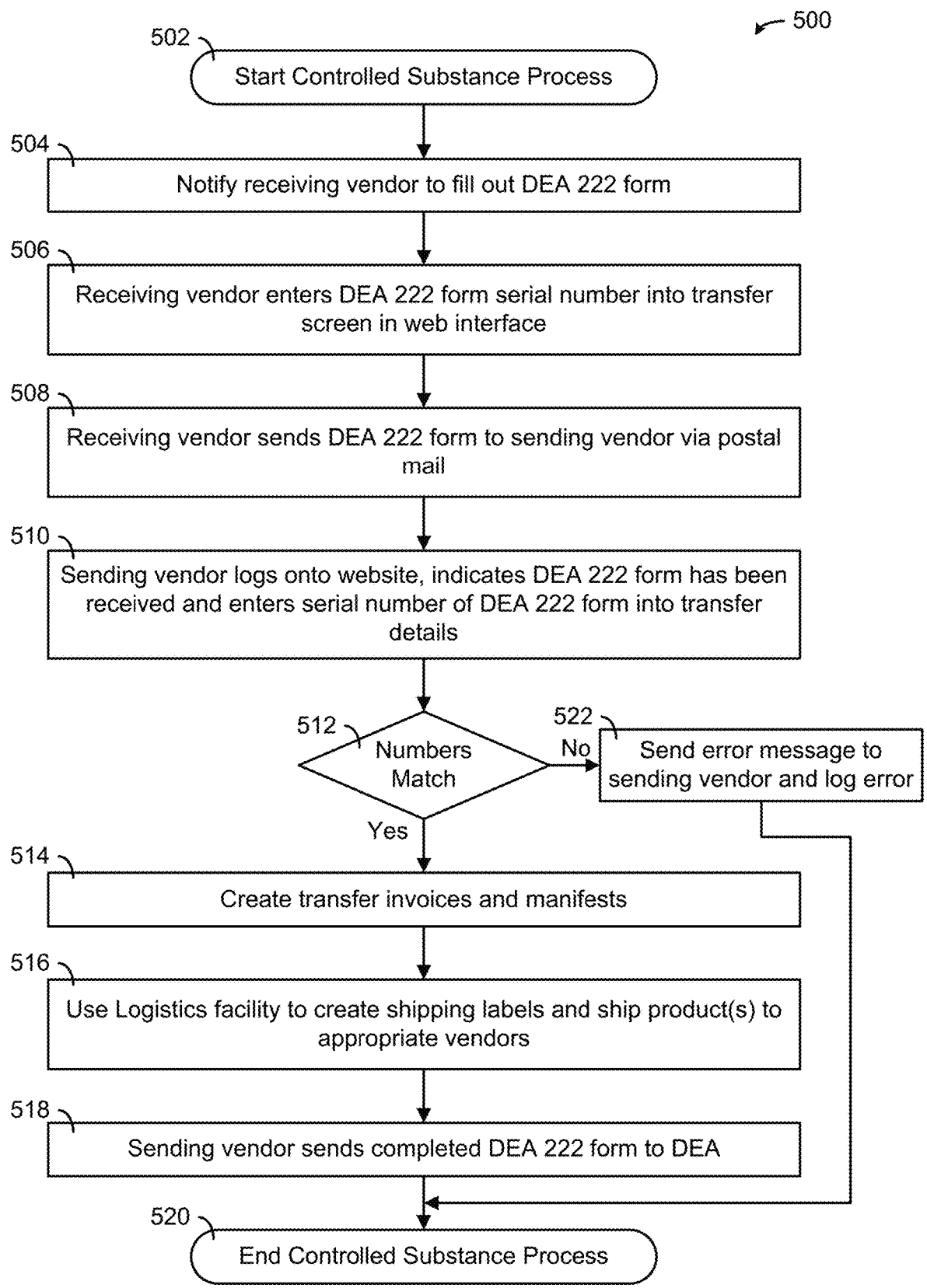
FIG. 5 is a flow chart of a controlled substance redistribution process in accordance with one embodiment of the present invention.

Referring now to FIG. 5, a flow chart of a controlled substance redistribution process 500 in accordance with one embodiment of the present invention is shown. The controlled substance redistribution process begins in block 502 and the receiving vendor is notified to fill out a DEA 222 form in block 504. The receiving vendor enters the DEA 222 form serial number into the transfer screen in a web interface of the present invention in block 506. The receiving vendor sends the DEA 222 form to the sending vendor via postal mail in block 508. The sending vendor logs onto the website of the present invention, indicates the DEA form has been received, and enters the serial number of the DEA 222 form into the transfer details in block 510. If the DEA 222 form serial numbers match, as determined in decision block 512, the transfer invoices and manifests are created in block 514. A logistics facility is used to create shipping labels and ship product(s) to the appropriate vendors in block 516. The sending vendor sends the completed DEA 222 form to the DEA in block 518 and the process ends in block 520. If, however, the DEA 222 form serial numbers do not match, as determined in decision block 512, an error message is sent to the sending vendor and the error is logged in block 522 so that the discrepancy can be resolved. Note that this process will also apply to other forms or other governmental entities.

Figure 6:
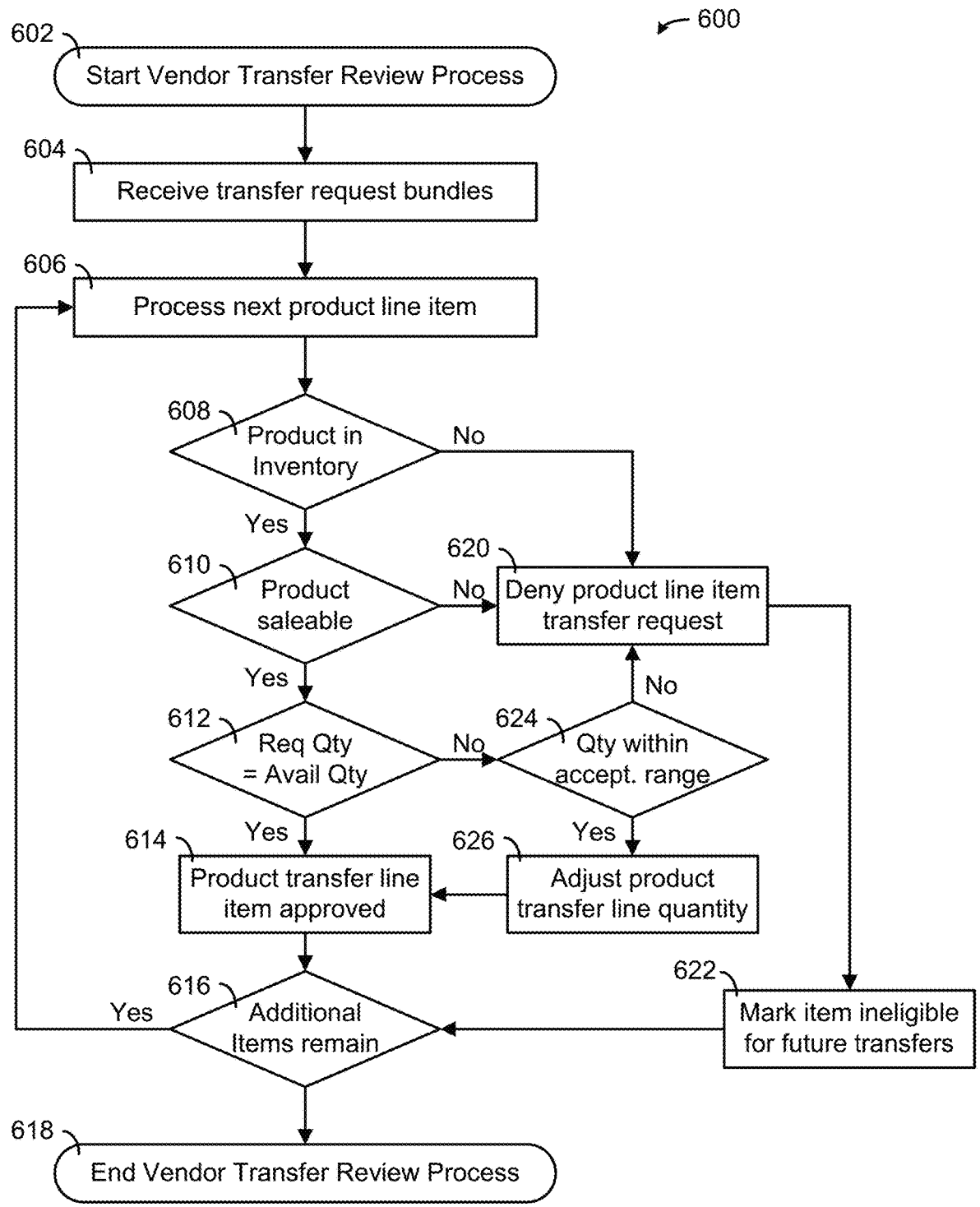
FIG. 6 is a flow chart of a vendor transfer review process in accordance with one embodiment of the present invention.

Now referring to FIG. 6, a flow chart of a vendor transfer review process 600 in accordance with one embodiment of the present invention is shown. The vendor transfer review process begins in block 602 and the vendor receives the transfer request bundles in block 604. The next product line item is processed in block 606. If the product is in inventory, as determined in decision block 608, the product is saleable, as determined in decision block 610, and the requested quantity of the product is equal to or less than the available quantity of the product in inventory, as determined in decision block 612, the product transfer line item is approved in block 614. If no additional items remain, as determined in decision block 616, the process ends in block 618. If, however, the product is not in inventory, as determined in decision block 608, or the product is not saleable, as determined in decision block 610, the product line item transfer request is denied in block 620, the item is marked as ineligible for future transfers in block 622, and the process continues to decision block 616. If, however, the requested quantity of the product is not equal to or less than the available quantity of the product in inventory, as determined in decision block 612, and the quantity is not within an acceptable range, as determined in decision block 624, the product lite item transfer request is denied in block 620 and the process continues as previously described. If, however, the quantity is within an acceptable range, as determined in decision block 624, the quantity of the product transfer line is adjusted in block 626, the product transfer line item is approved in block 614 and the process continues as previously described. If, however, additional items remain to be processed, as determined in decision block 616, the process loops back to process the next product line item in block 606 and repeats as previously described.

Figure 7:
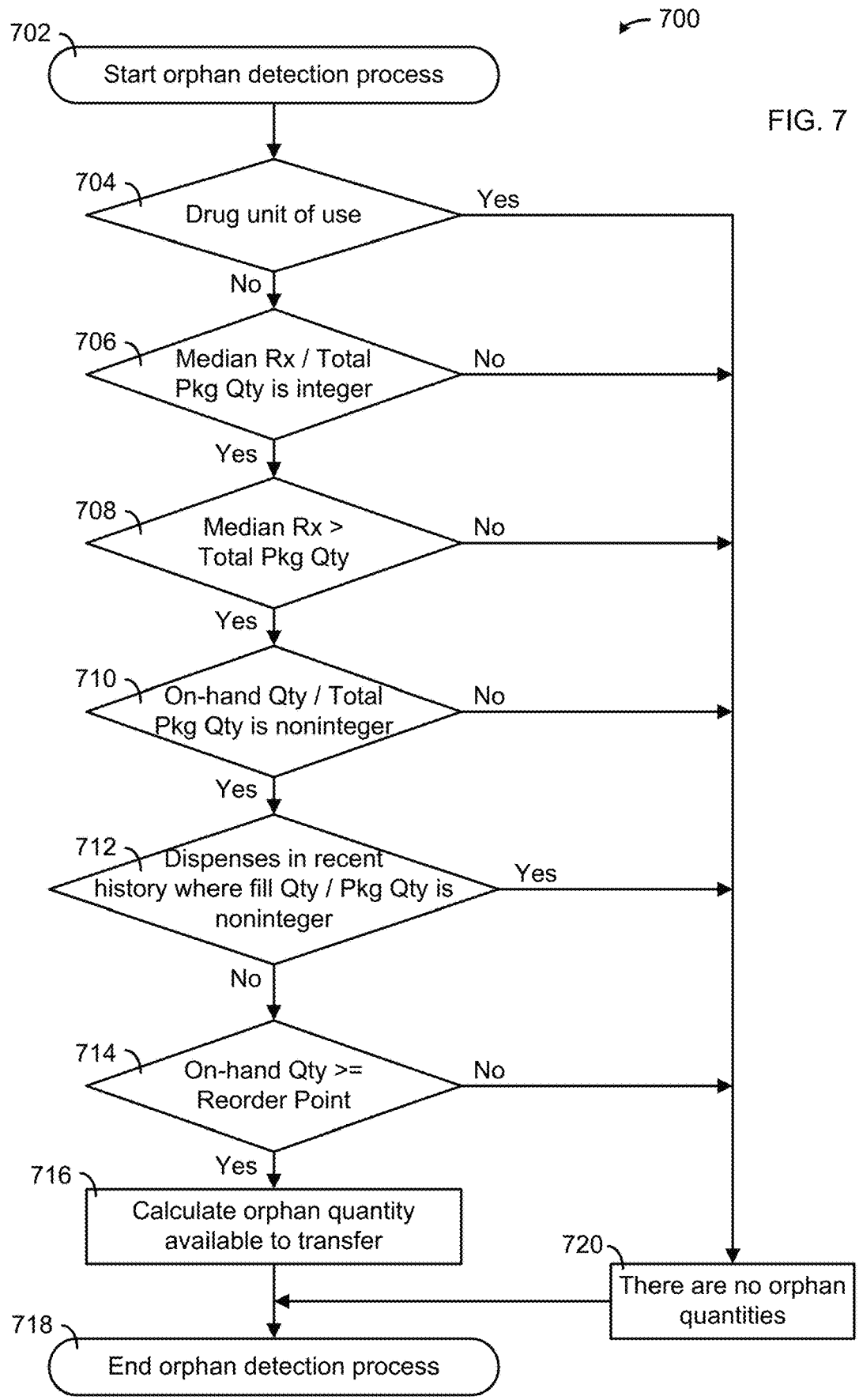
FIG. 7 is a flow chart of an orphan detection process in accordance with one embodiment of the present invention.

Referring now to FIG. 7, a flow chart of an orphan detection process 700 in accordance with one embodiment of the present invention is shown. The orphan detection process begins in block 702. If the drug unit is not of use, as determined in decision block 704, the median prescriptions divided by the total package quantity is an integer, as determined in decision block 706, the median prescriptions are greater than the total package quantity, as determined in decision block 708, the on-hand quantity divided by the total package quantity is a noninteger, as determined in decision block 710, the dispenses in recent history where the fill quantity divided by the package quantity is an integer, as determined in decision block 712, and the on-hand quantity is greater than or equal to a reorder point, as determined in decision block 714, the orphan quantity available for transfer is calculated in block 716 and the process ends in block 718.

If, however, the drug unit is of use, as determined in decision block 704, there are no orphan quantities in block 720 and the process ends in block 718. If, however, the median prescriptions divided by the total package quantity is not an integer, as determined in decision block 706, there are no orphan quantities in block 720 and the process ends in block 718. If, however, the median prescriptions are not greater than the total package quantity, as determined in decision block 708, there are no orphan quantities in block 720 and the process ends in block 718. If, however, the on-hand quantity divided by the total package quantity is an integer, as determined in decision block 710, there are no orphan quantities in block 720 and the process ends in block 718. If, however, the dispenses in recent history where the fill quantity divided by the package quantity is a noninteger, as determined in decision block 712, there are no orphan quantities in block 720 and the process ends in block 718. If, however, the on-hand quantity is not greater than or equal to a reorder point, as determined in decision block 714, there are no orphan quantities in block 720 and the process ends in block 718.

Figure 8:
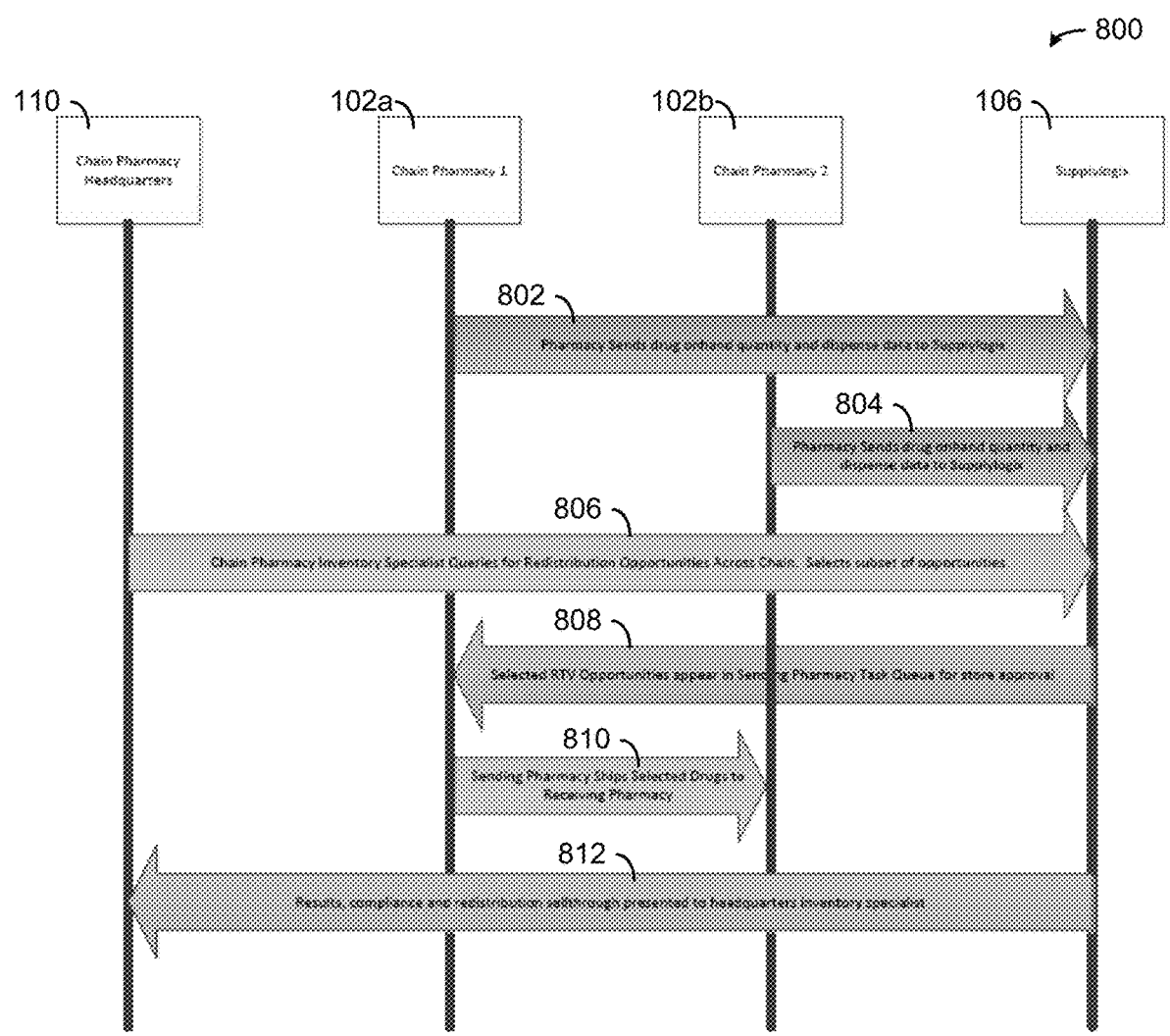
FIG. 8 is a flow chart of a product redistribution process in accordance with another embodiment of the present invention.

Now referring to FIG. 8, a flow chart of a product redistribution process 800 in accordance with another embodiment of the present invention is shown. In this example, Chain Pharmacy 1 (102*a*) and Chain Pharmacy 2 (102*b*) are members of a pharmacy chain having a Chain Pharmacy Headquarters 110. Supplylogix 106 provides and operates the present invention. Chain Pharmacy 1 (102*a*) sends drug on-hand quantities and dispense data to Supplylogix 106 in step 802. Chain Pharmacy 2 (102*b*) sends drug on-hand quantities and dispense data to Supplylogix 106 in step 804. The Chain Pharmacy Inventory Specialist 110 queries for redistribution opportunities across the chain and selects a subset of the opportunities in step 806. Selected redistribution opportunities, including return-to-vendor (supplier) opportunities, appear in the sending pharmacy task queue for store (vendor) approval in step 808. The sending pharmacy (e.g., Chain Pharmacy 1 (102*a*)) ships the selected drugs to the receiving pharmacy (e.g., Chain Pharmacy 2 (102*b*)) in step 810. The results, compliance and redistribution sell through are presented to the headquarters inventory specialist 110 in step 812.

Figure 9:
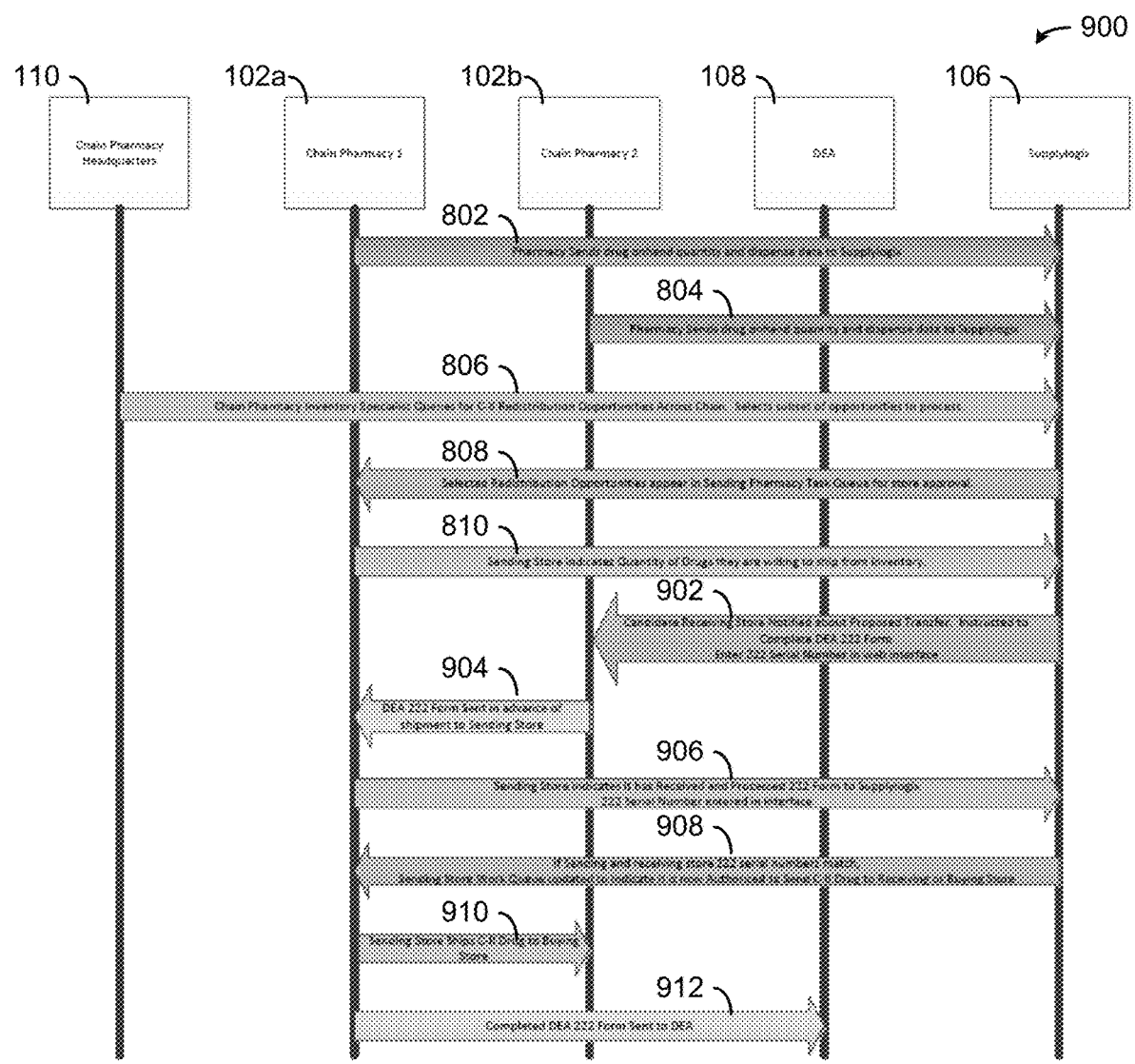
FIG. 9 is a flow chart of a controlled substance redistribution process in accordance with another embodiment of the present invention.

Referring now to FIG. 9, a flow chart of a controlled substance redistribution process 900 in accordance with another embodiment of the present invention is shown. In this example, Chain Pharmacy 1 (102*a*) and Chain Pharmacy 2 (102*b*) are members of a pharmacy chain having a Chain Pharmacy Headquarters 110. The DEA is a governmental entity 108 that monitors controlled substances. Supplylogix 106 provides and operates the present invention. Chain Pharmacy 1 (102*a*) sends drug on-hand quantities and dispense data to Supplylogix 106 in step 802. Chain Pharmacy 2 (102*b*) sends drug on-hand quantities and dispense data to Supplylogix 106 in step 804. The Chain Pharmacy Inventory Specialist 110 queries for redistribution opportunities across the chain and selects a subset of the opportunities in step 806. Selected redistribution opportunities, including return-to-vendor (supplier) opportunities, appear in the sending pharmacy task queue for store (vendor) approval in step 808. The sending pharmacy (e.g., Chain Pharmacy 1 (102*a*)) ships the selected drugs to the receiving pharmacy (e.g., Chain Pharmacy 2 (102*b*)) in step 810. The candidate receiving store (e.g., Chain Pharmacy 2 (102*b*)) is notified about the proposed transfer, instructed to complete DEA 222 form and enter the DEA 222 form serial number in the web interface in step 902. The candidate receiving store (e.g., Chain Pharmacy 2 (102*b*)) send the DEA 222 form to the sending store (e.g., Chain Pharmacy 1 (102*a*)) in advance of the shipment in step 904. The sending store (e.g., Chain Pharmacy 1 (102*a*)) indicates that it has received and processed the DEA 222 form to Supplylogix 106 and enters the DEA 222 form serial number into the web interface in step 906. If the sending (e.g., Chain Pharmacy 1 (102*a*)) and receiving store (e.g., Chain Pharmacy 2 (102*b*)) DEA 222 form serial numbers match, the sending store (e.g., Chain Pharmacy 1 (102*a*)) work queue is updated to indicate that it is now authorized to send the controlled substance to the receiving or buying store (e.g., Chain Pharmacy 2 (102*b*)) in step 908. The sending store (e.g., Chain Pharmacy 1 (102*a*)) then ships the controlled substance to the receiving or buying store (e.g., Chain Pharmacy 2 (102b)) in step 910, and sends the completed DEA 222 form to the DEA 108 in step 912. Note that this process can be easily modified to accommodate the requirements of other non-DEA governmental entities 108. Moreover, this embodiment of the present invention is not limited to any specific form required by the governmental entities 108. Finally, the form(s) required by the governmental entities 108 can be electronically generated, filled-in, transmitted and/or confirmed as allowed by the governmental entities 108.

Figure 10:
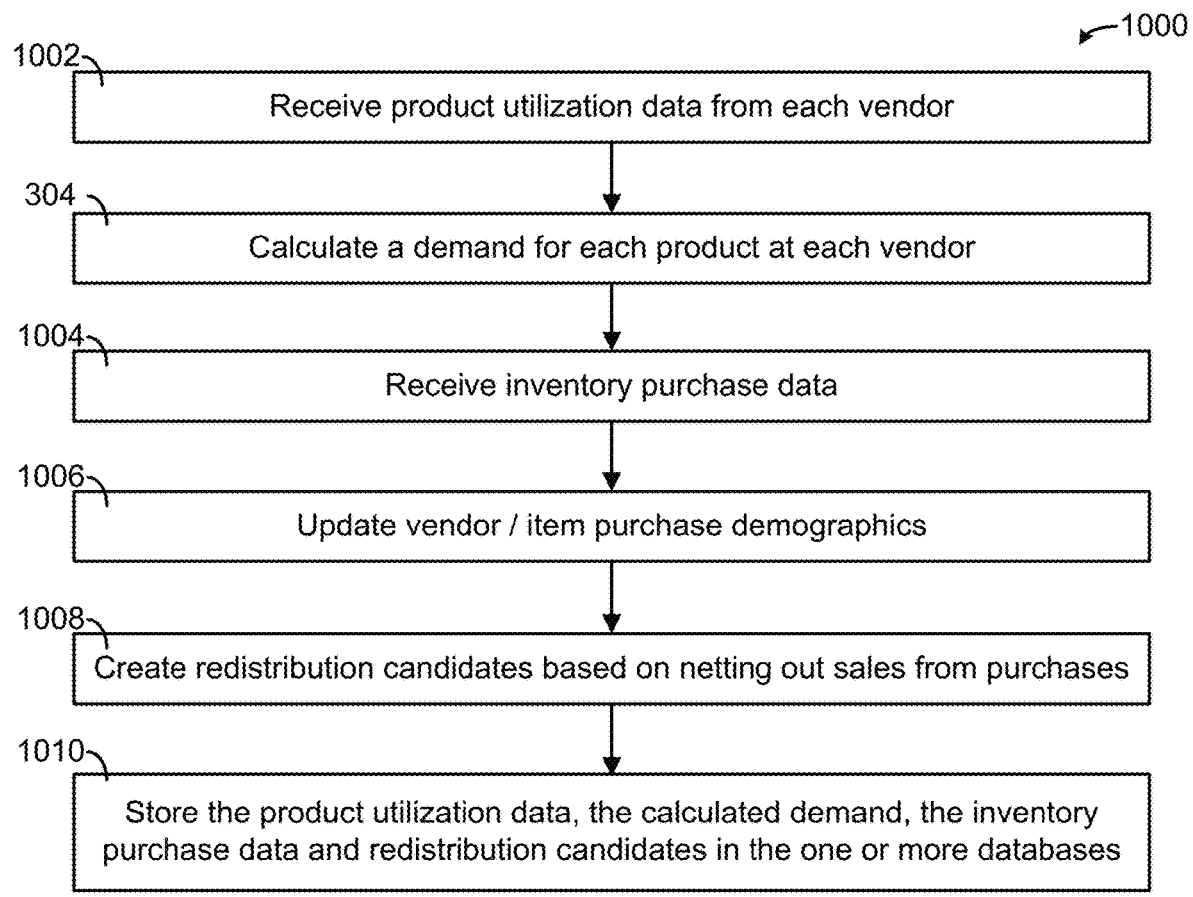
FIG. 10 is a flow chart of a database update process in accordance with another embodiment of the present invention.

Now referring to FIG. 10, a flow chart of a database update process 1000 in accordance with another embodiment of the present invention is shown. In some cases, the vendors do not maintain a perpetual inventory, so they do not have the on-hand quantity data readily available as used in previous examples of the present invention. In those cases, the present invention determines on-hand quantities and likely redistribution targets and amounts by netting dispenses from sales data. Product utilization data is received from each vendor in block 1002 and a demand is calculated for each product at each vendor in block 304. Inventory purchase data is received in block 1004 and vendor/item purchase demographics are updated in block 1006. Redistribution candidates are created based on netting out sales from inventory purchases in block 1008. The product utilization data, the calculated demand, the inventory purchase data and redistribution candidates are stored in the one or more databases in block 1010. Note that the foregoing method can be incorporated into the method described in FIG. 11 below. Moreover, the foregoing method can be implemented as a computer program embodied on a non-transitory computer readable medium for execution by a computer or processor such that the steps are implemented as one or more code segments.

Figure 11:
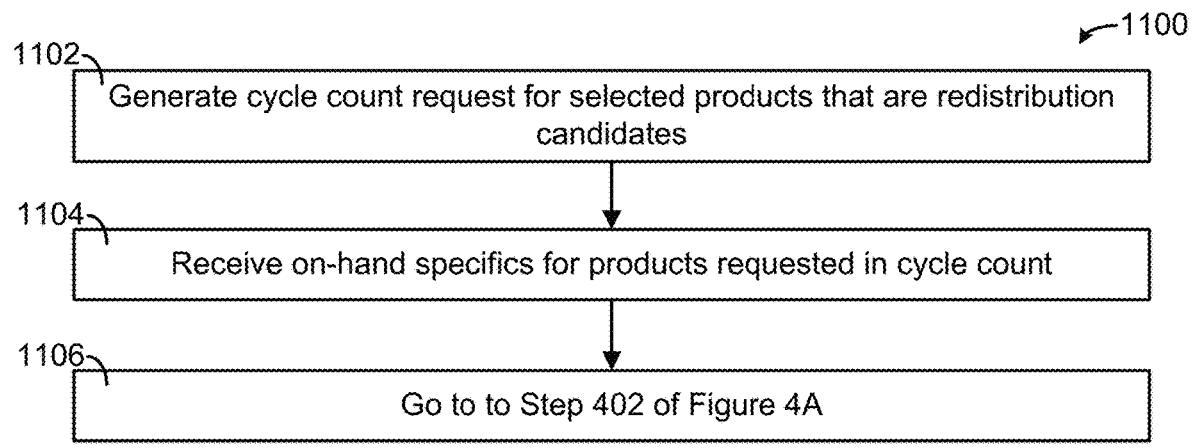
FIG. 11 is a flow chart of a product redistribution process in accordance with yet to another embodiment of the present invention.

Referring now to FIG. 11, a flow chart of a product redistribution process 1100 in accordance with yet another embodiment of the present invention is shown. A cycle count request for selected products that are redistribution candidates are generated in block 1102. On-hand specifics for products requested in the cycle count are received from the applicable vendors in block 1104. The process in block 1106 goes to block 402 of FIG. 4A and continues as previously described.

Figure 12:
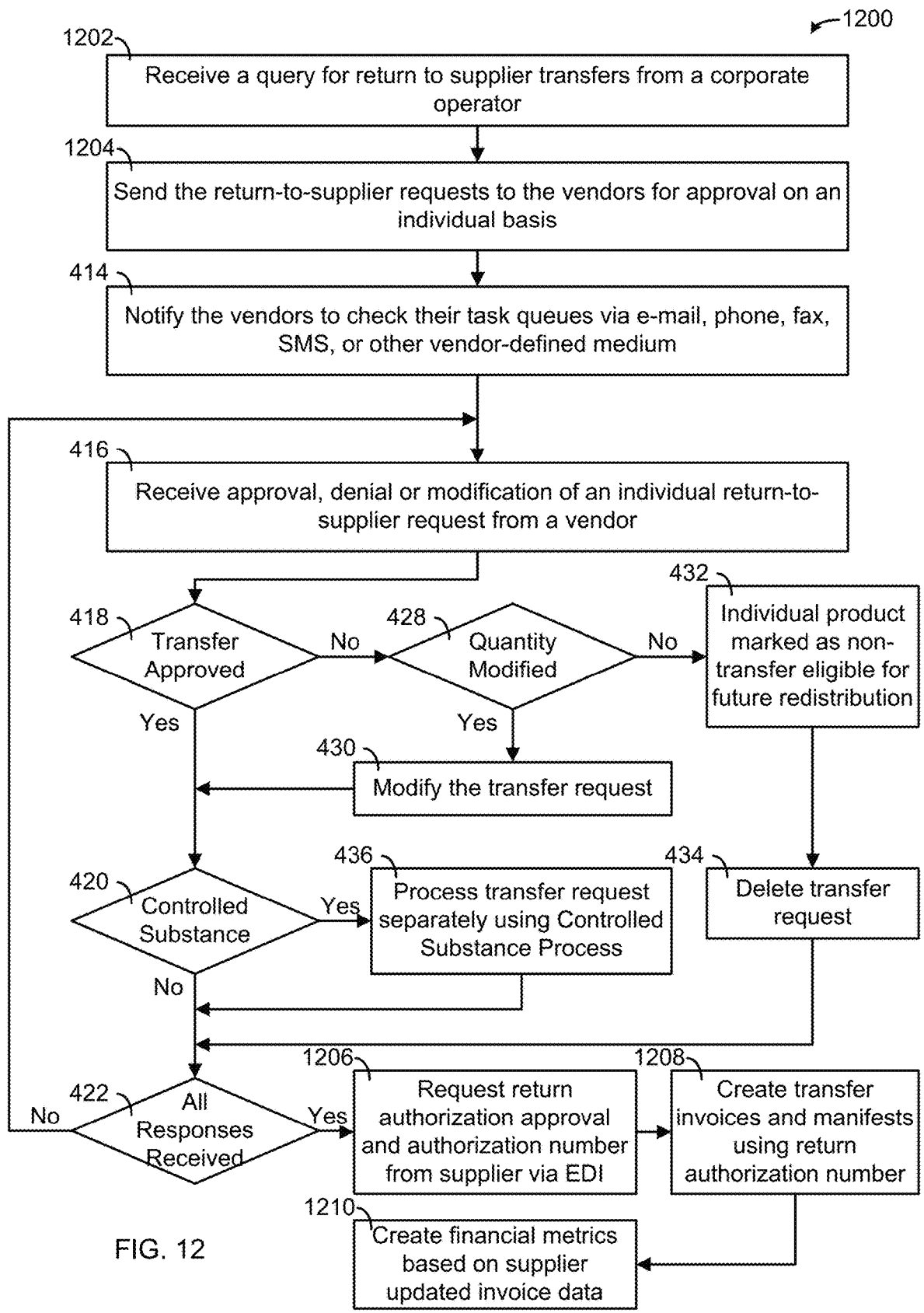
FIG. 12 is a flow chart of a return-to-supplier transfer process in accordance with another embodiment of the present invention.

Now referring to FIG. 12, a flow chart of a return-to-supplier transfer process 1200 in accordance with another embodiment of the present invention is shown. Note that the return-to-supplier transfer (also commonly referred to as return-to-vendor (RTV)) process can be implemented as transfer requests in the previously described methods or as a separate process as described in FIG. 12. A query for return-to-supplier transfers is received from a corporate operator in block 1202. The return-to-supplier transfer requests are sent to the vendors for approval on an individual basis in block 1204. The vendor approval process is shown and described in FIG. 6. The vendors are also notified to check their task queues via electronic mail, phone, fax, SMS, or other vendor-defined medium in block 414.

An approval, denial, or modification of an individual transfer is received from a vendor in block 416. If the transfer is approved, as determined in decision block 418, the product is not a controlled substance, as determined in decision block 420, and all the responses have been received, as determined in decision block 422, a return authorization approval and authorization number are requested from the supplier via EDI in block 1206. The transfer invoices and manifests are created using the return authorization number in block 1208. Financial metrics based on supplier updated invoice data are created in block 1210. If, however, the transfer is not approved, as determined in decision block 418, and the quantity is modified, as determined in decision block 428, the quantity in the transfer request is modified in block 430 and the process then proceeds to decision block 420. If, however, the quantity is not modified, as determined in decision block 428, the individual product is marked as non-transfer eligible for future redistribution in block 432, the transfer request is deleted in block 434 and the process then proceeds to decision block 422. If, however, the product is a controlled substance, as determined in decision block 420, the transfer request is processed separately in block 436 using the controlled substance process shown and described in FIG. 5. If, however, all responses have not been received, as determined in decision block 422, the process loops back to block 416 where the next approval, denial or modification of the individual transfer is received and processed as previously described. Note that at some point, the system may send reminders or prompt vendors that have not responded to the individual transfer requests. "Stale" or individual transfer requests that have not be processed by the individual vendors may also be assumed to be denied and deleted after a specified period of time.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present invention have been described in detail, it will be understood by those skilled in the art that various modifications can be made therein without departing from the spirit and scope of the invention as set forth in the appended claims.

What is claimed is:

1. A computerized method for managing a product inventory of two or more vendors using a computer having a communications interface and one or more processors communicably coupled to the interface and one or more databases, the method comprising the steps of:
   determining each slow or non-moving product at each vendor based on a product utilization data and a product inventory data using the one or more processors;

generating one or more product transfers by matching a demand for each product at each vendor based on the product utilization with the slow or non-moving products at other vendors using the one or more processors;

bundling the one or more product transfers by vendor-to-vendor pairings using the one or more processors, wherein each vendor-to-vendor pairing comprises a sending vendor and a receiving vendor;

automatically creating and sending one or more transfer orders to a vendor device of each sending vendor identified in the transfer bundles via the communications interface of the computer;

shipping the products from the sending vendor to the receiving vendor in accordance with the one or more transfer orders; and wherein all communications with the communications interface are encrypted.

2. The method as recited in claim 1, wherein:

the vendor comprises a retailer, a wholesaler or a distributor;

the database comprises a first database for the product inventory data, a second database for the product utilization data, and a third database for the transfer bundles;

the product inventory data comprises a product name and a quantity available; or the product utilization data comprises the product name, a customer identifier, a sales date and a quantity sold.

3. The method as recited in claim 1, wherein the one or more transfer orders comprise one or more invoices, one or more manifests, one or more shipping labels, or a combination thereof.

4. The method as recited in claim 1, wherein the product utilization data does not include any personal data.

5. The method as recited in claim 1, further comprising the step of receiving the product inventory data and the product utilization data from each vendor.

6. The method as recited in claim 5, wherein the product inventory data and the product utilization data is received from each vendor on a daily basis.

7. The method as recited in claim 5, wherein the product inventory data and the product utilization data are received from each vendor in real-time or near real-time.

8. The method as recited in claim 1, further comprising the step of receiving one or more queries for product transfers from a device of an inventory manager for one of the vendors.

9. The method as recited in claim 1, wherein the one or more product transfers are further based on a product availability, a logistics cost and one or more legal compliance rules.

10. The method as recited in claim 1, wherein the one or more product transfers are further bundled to decrease a logistics cost and maximize a value of the product transfer.

11. The method as recited in claim 1, further comprising the steps of:

providing the one or more transfer bundles to a device of an inventory manager for all of the two or more vendors for a final selection or an approval;

receiving the final selection or the approval of the one or more transfer bundles from the device of the inventory manager, and wherein the transfer bundles sent to the device of the inventor manager comprise the final selection or the approval of the one or more transfer bundles; and providing one or more results of the transfer orders, one or more results of the transfer bundles, a compliance data or a redistribution sell through data to the device of the inventory manager.

12. The method as recited in claim 1, further comprising the step of removing any transfer bundles that no longer meet one or more defined minimum value thresholds.

13. The method as recited in claim 1, further comprising the step of notifying each sending vendor to approve, modify or deny the transfer bundles via electronic mail, phone, fax, SMS or other vendor-defined medium.

14. The method as recited in claim 1, further comprising the step of receiving a notification from a vendor device of one of the vendors that one of the products in the transfer bundle is ineligible for transfer.

15. The method as recited in claim 1, wherein the transfer bundle is denied whenever the product is not present in the inventory, the product is not for sale, a quantity of the product is not within an acceptable range.

16. The method as recited in claim 1, wherein the vendor-to-vendor transfer further comprises a return-to-supplier transfer.

17. The method as recited in claim 16, further comprising the steps of:

requesting a return authorization approval and a return authorization number from a supplier, a wholesaler or a manufacturer of the product via the communications interface; and wherein the transfer order for the return-to-supplier transfer is created using the return authorization number.

18. The method as recited in claim 1, wherein the products comprise one or more pharmaceuticals.

19. The method as recited in claim 18, further comprising the step of determining whether there are any orphan quantities of the one or more pharmaceuticals at each vendor using the one or more processors.

20. The method as recited in claim 19, wherein the step of determining whether there are any orphan quantities of the one or more pharmaceuticals at each vendor comprises the step of calculating the orphan quantities available for transfer at each vendor whenever (a) a median prescription divided by a total package quantity is an integer, (b) the median prescription is greater than the total package quantity, (c) an on-hand quantity divided by the total package quantity is not the integer, (d) a number of dispenses in recent history where the fill quantity divided by the total package quantity is the integer, and (e) the on-hand quantity is greater than or equal to a reorder point.

21. The method as recited in claim 18, wherein one of the one or more pharmaceuticals comprises a controlled substance, and further comprising the steps of:

notifying the vendor device of the receiving vendor of the controlled substance to fill out one or more forms required by a governmental entity and send the completed one or more forms to a vendor device of the sending vendor the controlled substance;

receiving an identification number for the completed one or more forms from the vendor device of the receiving vendor of the controlled substance; and receiving an indication from the vendor device of the sending vendor that the vendor sending the controlled substance has received the completed one or more forms.

22. The method as recited in claim 18, wherein:

the product inventory data comprises a vendor identifier, a drug name or code, a generic equivalent name, a strength, a package size, a quantity available, and an inventory level based on the quantity available and the package size; and the product utilization data comprises the vendor identifier, a sales date, a drug name or code, a quantity sold, a fill number and a customer identifier.

23. The method as recited in claim 1, further comprising the steps of:

receiving a product transfer request from the vendor device of a first vendor, wherein the product transfer request identifies the product and a second vendor; and sending the product transfer request to the vendor device of the second vendor via the communications interface.

24. The method as recited in claim 23, further comprising the step of rejecting the product transfer request whenever the product transfer request does not meet one or more defined minimum value thresholds.

25. The method as recited in claim 23, further comprising the steps of:

receiving an approval, a modification or a denial of the product transfer request from the vendor device of the second vendor; and creating one or more transfer orders for the product transfer request whenever the approval or the modification of the product transfer request is received.

26. An apparatus comprising:

a communications interface;

a memory;

one or more databases; and one or more processors communicably coupled to the communications interface, the memory and the one or more databases wherein the one or more processors:

determine each slow or non-moving product at each vendor based on a product utilization data and a product inventory data using the one or more processors;

generate one or more product transfers by matching a demand for each product at each vendor based on the product utilization with the slow or non-moving products at other vendors using the one or more processors;

bundle the one or more product transfers by vendor-to-vendor pairings using the one or more processors, wherein each vendor-to-vendor pairing comprises a sending vendor and a receiving vendor;

automatically create and send one or more transfer orders to a vendor device of each sending vendor identified in the transfer bundles via the communications interface;

shipping the products from the sending vendor to the receiving vendor in accordance with the one or more transfer orders; and wherein all communications with the communications interface are encrypted.

27. A system comprising:

one or more vendor devices;

one or more communication networks;

a data processing device comprising:

a communications interface communicably coupled to the one or more vendor devices via the one or more communication networks, a memory, one or more databases, and one or more processors communicably coupled to the communications interface, the memory and the one or more databases wherein the one or more processors:

determine each slow or non-moving product at each vendor based on a product utilization data and a product inventory data using the one or more processors;

generate one or more product transfers by matching a demand for each product at each vendor based on the product utilization with the slow or non-moving products at other vendors using the one or more processors;

bundle the one or more product transfers by vendor-to-vendor pairings using the one or more processors, wherein each vendor-to-vendor pairing comprises a sending vendor and a receiving vendor;

automatically create and send one or more transfer orders to a vendor device of each sending vendor identified in the transfer bundles via the communications interface;

shipping the products from the sending vendor to the receiving vendor in accordance with the one or more transfer orders; and wherein all communications with the communications interface are encrypted.

28. A non-transitory computer readable medium for managing a product inventory of two or more vendors, comprising instructions stored thereon, that when executed by a computer having an interface, one or more databases and one or more processors communicably coupled to the interface and one or more databases, perform the steps comprising:

determining each slow or non-moving product at each vendor based on a product utilization data and a product inventory data using the one or more processors;

generating one or more product transfers by matching a demand for each product at each vendor based on the product utilization with the slow or non-moving products at other vendors using the one or more processors;

bundling the one or more product transfers by vendor-to-vendor pairings using the one or more processors, wherein each vendor-to-vendor pairing comprises a sending vendor and a receiving vendor;

automatically creating and sending one or more transfer orders to a vendor device of each sending vendor identified in the transfer bundles via the communications interface of the computer;

shipping the products from the sending vendor to the receiving vendor in accordance with the one or more transfer orders; and wherein all communications with the communications interface are encrypted.

\* \* \* \* \*